United States Patent [19]

Chwalisz et al.

[11] Patent Number: 6,143,754

[45] Date of Patent: Nov. 7, 2000

[54] COMPETITIVE PROGESTERONE ANTAGONIST FOR DEMAND-ORIENTED FEMALE BIRTH CONTROL

[75] Inventors: Kristof Chwalisz; Klaus Stockemann; Karin Schmidt-Gollwitzer; Walter Klemann, all of Berlin, Germany

[73] Assignee: Schering Aktiengesellschaft, Berlin, Germany

[21] Appl. No.: 09/273,485

[22] Filed: Mar. 22, 1999

Related U.S. Application Data

[63] Continuation of application No. 08/817,535, Jul. 22, 1997, abandoned.

[30] Foreign Application Priority Data

Oct. 24, 1994 [DE] Germany .............................. 44 38 820

[51] Int. Cl.[7] .......................... A61K 31/435; A61K 31/13
[52] U.S. Cl. ........................... 514/277; 514/579; 514/843
[58] Field of Search ................................... 514/277, 579, 514/843

[56] References Cited

U.S. PATENT DOCUMENTS 5,439,913   8/1995   Chwalisz et al. ....................... 514/277

FOREIGN PATENT DOCUMENTS 9323020   11/1993   WIPO .

OTHER PUBLICATIONS

Experimental and Clinical Endocrinology, vol. 81, No. 2, 1983, pp. 122–136, Strecke, J. et al.

Journal of Steroid Biochemistry, vol. 11, No. 1C, 1979, pp. 963–969, Csapo, A.I. et al.

The New England Journal of Medicine, vol. 316, No. 4, 1987, pp. 187–191, Nieman, L.K. et al.

Human Reproduction, vol. 9, No. 2, Jun. 1994, pp. 11–21, Lebeau, M.C. et al.

European Journal of Obstetrics, Gynaecology and Reproductive Biology, vol. 4, No. 5, 1975, pp. 161–166, Baulieu, E.E.

International Search Report for PCT/EP95/04191 mailed Mar. 22, 1996.

*Primary Examiner*—Kevin E. Weddington
*Attorney, Agent, or Firm*—Millen, White, Zelano & Branigan, P.C.

[57] ABSTRACT

This invention describes the novel use of dissociated competitive progesterone antagonists for the production of a pharmaceutical agent for demand-oriented female birth control (pill on demand), which can be used regardless of the point in the menstrual cycle, in a dosage unit that is to be administered on a one-time basis, whose dosage is below the ovulation-inhibiting dosage.

10 Claims, No Drawings

COMPETITIVE PROGESTERONE ANTAGONIST FOR DEMAND-ORIENTED FEMALE BIRTH CONTROL

This application is a continuation of Ser. No. 08/817,535 filed Jul. 22, 1997; now abandoned.

This invention relates to the use of at least one competitive progesterone antagonist for the production of a pharmaceutical agent for demand-oriented female birth control ("pill on demand"), which can be used at any point in the menstrual cycle, in a dosage unit that is to be administered on a one-time basis, whose dosage is below the ovulation-inhibiting dosage.

Already all over the world, the use of oral contraceptives has developed into a business factor that cannot be ignored. Especially in view of the fact that the world population is continuing to shoot upward, further development of the hitherto proven methods for birth control is absolutely necessary.

The use of competitive progesterone antagonists in female birth control both in various animal species and in humans has been discussed for some years now, as can be found in the publications listed below, whereby especially the use of RU 486 (11-β-[4-N,N-(dimethylamino)phenyl]-17-β-hydroxy-17-α-propinylestra-4,9(10)-dien-3-one; EP-A-0057115) has been cited in this connection:

Collins et al., Blockade of the Spontaneous Mid-Cycle Gonadotrophin Surge in Monkeys by RU 486; A Progesterone Antagonist or Agonist. J. Cli. Metab., 63: 1270–1276 (1986);

Croxatto, H. B., Salvatierra 1990 Cyclic Use of Antigestagens for Fertility Control. IIIrd International Symposium on Contraception, Heidelberg, Jun. 19–23, 1990;

Danford et al., Contraceptive Potential of RU 486 by Ovulation Inhibition. III. Preliminary Observations on Once Weekly Administration. Contraception 40: 195–200 (1989);

Kekkonen et al., Lähteoenmäki P 1990 Interference with Ovulation by Sequential Treatment with the Antiprogesterone RU 486 and Synthetic Progestin. Fertil Steril [Fertile Sterile] 53: 4747 (1990);

Puri et al., Gonadal and Pituitary Responses to Progesterone Antagonist ZK 98 299 during the Follicular Phase of the Menstrual Cycle in Bonnet Monkeys. Contraception 39(2): 227–243 (1989);

Puri et al., Contraceptive Potential of a Progesterone Antagonist ZK 98 734: Effect on Folliculogenesis, Ovulation and Corpus Luteum Function in Bonnet Monkeys. In Moudgal et al., (eds) (1990).

In this connection, it should be mentioned that the dosage that exerts an ovulation-inhibiting effect depends to a great extent on the competitive progesterone antagonist that is used.

The class of 11β-aryl- or 11β,19-arylene-substituted steroids is distinguished pharmacologically according to their strong progesterone- or glucocorticoid-antagonistic effect. Thus, RU 468 can be used, on the one hand, to bring about a therapeutically induced abortion (the human abortive dosage in combination with a prostaglandin is approximately 200–600 mg; EP-A 0 139 608), but also, on the other hand, via its antagonistic effect on a glucocorticoid receptor, to treat Cushing's syndrome.

Another possible use of competitive progesterone antagonists for female birth control, the so-called "LH+2" treatment, is proposed by Swahn et al. [The Effect of RU 486 Administration During the Early Luteal Phase on Bleeding Pattern, Hormonal Parameters and Endometrium, Human Reproduction 5(4): 402–408 (1990)], by an ovulation-inhibiting RU 486 dosage unit being administered (luteal contraception) one time 2 days after the increase in the luteinizing hormone (LH) in the female menstrual cycle (this is generally on day 14, 15 or 16).

This process has no practical importance, however, since determining the LH peak in a simple and precise manner still represents a problem.

Glasier et al. (Mifepristone (RU 486) Compared with High-Dose Estrogen and Progestogen for Emergency Postcoital Contraception, The New England J. of Med. 327: 1041–1044 (1992)] also describes the use of RU 486 for postcoital contraception (emergency postcoital contraception). The method shows a low level of side effects in addition to high effectiveness. An extension of the cycle occurred in a high percentage of women in this study. This effect can be attributed primarily to the antiovulatory effect of RU 486.

In addition, WO 93/23020 describes that competitive progesterone antagonists at a dose that lies both below the abortive and ovulation-inhibiting dosage can be used for female birth control. Here, however, generally weekly or repeated and thus regular administration is necessary to achieve the desired effect.

EP-A 0 219 447 also describes what effects the daily administration of a progesterone antagonist triggers with respect to the endometrial differentiation state during the follicular phase or optionally also the luteal phase of the female cycle in a period of up to 4 days at a dosage of 10–200 mg. The changes in the endometrium that result in this connection are used with respect to the time of nidation for in vitro fertilization.

Batista et al. [Daily Administration of the Progesterone Antagonist RU 486 Prevents Implantation in the Cycling Guinea Pig. Am. J. Obstet. Gynecol. 165:82–86 (1991)] also describes the use of RU 486 for female birth control, which in an ovulation-inhibiting dosage prevents nidation in guinea pigs by daily intake, precoitally and throughout the entire further cycle.

Kawano et al. (Effect of RU 486 on Glycogen Metabolism in Endometrium. Acta Obstetrica et Gynaecologica Japonica, 41: 1507–1511, (1989)] describes the influence of RU 486 at a dosage of 30 mg/kg of body weight on the endometrial glycogen metabolism in a rat model, so that successful implantation is disrupted. Administration is done, however, on day 2 or 4 of the pregnancy.

It has now been found, surprisingly enough, that nidation can be reliably prevented by even one-time administration only upon demand of a competitive progesterone antagonist (at a subovulation-inhibiting dosage), and in this respect a new type of oral contraceptive is available.

Previously, the use of competitive progesterone antagonists for contraception was possible only by repeated, regular intake.

Also, previous usage according to EP-A 0 219 447 is in contrast to this invention since here nidation should be made possible specifically by the administration of progesterone antagonist.

A so-called dissociated competitive progesterone antagonist is suitably used according to the invention.

In this connection, a dissociated, competitive progesterone antagonist is defined as a substance that at the dosage used exerts its action via the hypothamalic-ovarian axis not in terms of ovulation inhibition (central effect), but rather a local effect (peripheral selective effect) that is limited exclusively to the endometrium.

Right at a certain threshold dose, changes in the endometrium are observed while ovulation is not inhibited.

The quotient of ovulation-inhibiting and implantation-inhibiting dose (dissociation factor) can be used as a yardstick for the dissociation. Said quotient varies depending on the species.

In rats and in primates, all previously studied competitive progesterone antagonists show a dissociation between central and endometrial effects. The extent of this dissociation is substance-dependent. For a dissociated, competitive progesterone antagonist that is to be used according to the invention (found in the rat after peroral administration), the dissociation factor should preferably lie approximately at 30 or above.

RU 486 is an example of a slightly dissociated substance in primates. It inhibits ovulation even at low doses and thus results in cycle disruption.

Onapristone (11β-[4-N,N-(dimethylamino)phenyl]-17α-hydroxy-17β-(3-hydroxypropyl)-13α-methyl-4,9(10)-gonadien-3-one; EP-A 0 129 499) is an example of a greatly dissociated progesterone-antagonistic compound that inhibits ovulation in primates only at extremely high doses.

The endometrial effects of RU 486 and Onapristone occur, however, at comparable doses. This dissociation between central and endometrial effects makes it possible, when using a dissociated, competitive progesterone antagonist for the purposes of this invention, to increase its dosage and thus to ensure effective implantation inhibition after a single use.

In this respect, with the solution according to the invention, another requirement that is to be imposed on modern pharmaceutical agents is also that systemic loading of the organism by one-time administration be avoided by a locally differentiated mode of action.

The above statements make it clear that demand-oriented oral birth control was not possible until now.

Specifically for women who could not decide on the previously necessary, uniform intake of oral contraceptives or else for other, e.g., medicinal reasons, did not have the option of selecting this form of birth control, there now exists the alternative of opting for the one-time, demand-oriented intake of an oral contraceptive, without the organism having to be exposed to a hormonal control that continues throughout the entire menstrual cycle.

This invention has additional significant advantages, which certainly include the low dosage of the active ingredient.

Thus, the female menstrual cycle is in no way adversely affected in its cyclicity (as is caused by ovulation-inhibiting substances), and the organism is not stressed by unnecessarily large amounts of the competitive progesterone antagonist.

The use of such a progesterone antagonist further offers reliable contraception, i.e., the one-time intake of such a medicine prevents the nidation of the blastocysts.

According to this invention, the competitive progesterone antagonists are used in amounts of generally 1–400 mg of Onapristone or a biological equivalent dose of another competitive progesterone antagonist on a one-time basis.

Treatment with the competitive progesterone antagonist is generally performed regardless of the cycle time by the one-time, demand-oriented, i.e., generally precoital or else postcoital intake of a daily dosage unit.

Precoital intake of the medicine that is produced according to the invention is preferred. The time of intake can be up to 6 hours before or up to 24 hours after coitus.

In this case, intake is possible at any cycle time when a contraceptive measure is necessary, advisable, or desired.

As competitive progesterone antagonists, all compounds according to the invention that show a corresponding characteristic affinity for the progesterone receptor and exert an endometrium-selective effect are suitable. Such progesterone antagonists show nidation inhibition at the dosage used without inhibiting the ovulation. Thus, for example, the following progesterone antagonists are suitable:

11β-[4-N,N-(Dimethylamino)phenyl]-17α-hydroxy-17β-(3-hydroxypropyl)-13α-methyl-4,9(10)-gonadien-3-one (EP-A 0 129 499), 11β-[4-acetylphenyl]-17β-hydroxy-17α-(3-hydroxyprop-1(Z)enyl)-4,9(10)-estradien-3-one (EP-A 0 190 759), 11β,19-[4-(cyanophenyl)-o-phenylene]-17β-hydroxy-17α-(3-hydroxyprop-1(Z)-enyl)-4-androsten-3-one, 11β,19-[4-(3-pyridinyl)-o-phenylene]-17β-hydroxy-17α-(3-hydroxyprop-1(Z)-enyl)-4-androsten-3-one (both WO-A 93/23020), 17α-hydroxy-17β-(3-hydroxypropyl)-11β-[4-(1-methylethenyl)-phenyl]-13α-estra-4,9-dien-3-one, 11β-[4-(3-furanyl)phenyl]-17α-hydroxy-17β-(3-hydroxypropyl)-13α-estra-4,9-dien-3-one (both EP-A 0 349 481), (Z)-11β-[4-(dimethylamino)phenyl]-17β-hydroxy-17α-(3-hydroxyprop-1-enyl)estr-4-en-3-one (EP-A 0 404 283), 11β-[4-[[(acetyloxy)imino]methyl]phenyl]-17β-methoxy-17α-(methoxymethyl)estra-4,9-dien-3-one (EP-A 0 648 778, EP-A 0 648 779), 11β-[4-[[[[(ethoxycarbonyl)oxy]imino]methyl]phenyl]-17β-methoxy-17α-(methoxymethyl)estra-4,9-dien-3-one (EP-A 0 648 778, EP-A 0 648 779), 11β-[4-(acetyl)phenyl]-19,24-dinor-17,23-epoxy-17α-chola-4,9,20-trien-3-one, (11β,17α)-11-[4-(acetyl)phenyl]-17,23-epoxy-19,24-dinorchola-4,9,20-trien-3-one.

The competitive progesterone antagonists can be administered, for example, locally, topically, enterally, or parenterally.

For the preferred oral administration, especially tablets, coated tablets, capsules, pills, suspensions, or solutions that can be produced in the usual way with the additives and vehicles that are commonly used in galenicals are suitable.

The oral dosage unit that is to be administered on a one-time basis contains about 2 to 200 mg of Onapristone or the biologically equivalent dose (equivalent-action amount) of another dissociated competitive progesterone antagonist.

The dose that induces premature menstruation in Cynomolgus monkeys after one-time treatment on day 22 of the cycle but does not inhibit ovulation if administered on a one-time basis before the LH peak (LH-2) is considered an equivalent-action amount.

Particularly in the case of the preferred oral administration of the pharmaceutical agent that is produced according to the invention, it is desirable that a delayed release of the respective active ingredient occur. As a result, it is to be ensured that delayed implantation of the fertilized egg cannot occur.

Delayed release of the competitive progesterone antagonist can be achieved, for example, by formulating the dosage unit that is to be administered orally as a composite tablet or by providing the dosage unit that is to be administered orally with a timed-disintegration coating, as is readily known to one skilled in the art. The competitive progesterone antagonist that is used for the production of the pharmaceutical agent according to the invention can, by derivatization, for example, by esterification of a free hydroxy group in an effective precursor, also exhibit a longer half-life than this precursor. As a result, a prolonged effect is also achieved. This principle is implemented in, for example, the esters of 11β-[4-N,N(dimethylamino)phenyl]-17α-hydroxy-17β-(3-hydroxypropyl)-13α-methyl-4,9(10)-gonadien-3-one (Onapristone) described in EP-A 0186 834, which are therefore preferably used within the scope of this invention. The following can be mentioned as representatives:

17β-(3-Acetoxypropyl)-11β-[4-N,N-(dimethylamino)phenyl]-17α-hydroxy-13α-methyl-4,9(10)-gonadien-3-one and 17β-(3-benzoyloxypropyl)-11β-[4-N,N-(dimethylamino)phenyl]-17α-hydroxy-13α-methyl-4,9(10)-gonadien-3-one.

In addition, for local or topical use, for example, vaginal suppositories or transdermal systems such as skin plasters are available.

The dosage unit that is to be administered on a one-time basis contains an amount of Onapristone or a biologically equivalent dose of another competitive progesterone antagonist for this special form of administration such that over a period of 4 to 72 hours, 1 to 400 mg of this competitive progesterone antagonist is released.

The examples below are to explain the formulation of a competitive progesterone antagonist, which is of special relevance for use within the scope of this invention.

EXAMPLE 1

Composition of a tablet with 10.0 mg of 11β-[(4-N,N-dimethylamino)-phenyl]-17α-hydroxy-17β-(3-hydroxypropyl)-13α-methyl-4,9-gonadien-3-one for oral administration 10.0 mg of 11β-[(4-N,N-dimethylamino)-phenyl]-17α-hydroxy-17β-(3-hydroxypropyl)-13α-methyl-4,9-gonadien-3-one 140.5 mg of lactose 69.5mg of corn starch 2.5mg of poly-N-vinylpyrrolidone 2.0mg of aerosil 0.5mg of magnesium stearate 225.0mg total weight of the tablet

EXAMPLE 2

Composition of a tablet with 50.0 mg of 11β,19-[4-(cyanophenyl)-o-phenylene]-17β-hydroxy-17α-(3-hydroxyprop-1(Z)-enyl)-4-androsten-3-one for oral administration 50.0 mg of 11β,19-[4-(Cyanophenyl)-o-phenylene]-17β-hydroxy-17α-(3-hydroxyprop-1(Z)-enyl)-4-androsten-3-one 140.5 mg of lactose 69.5 mg of corn starch 2.5 mg of poly-N-vinylpyrrolidone 2.0 mg of aerosil 0.5 mg of magnesium stearate 265.0 mg total weight of the tablet The tablets are produced in a known way on a tablet press and are provided with a timed-disintegration coating.

Pharmacological Observations

The suitability especially of dissociated competitive progesterone antagonists for the production of a pharmaceutical agent for demand-oriented female birth control ("pill on demand"), which can be administered on a one-time basis in a non-ovulation-inhibiting dosage of the competitive progesterone antagonist, follows from the animal-experimental and human-pharmacological observations described below:

Cyclic female monkeys (body weight about 4–5 kg) are treated one time over 3 cycles in the late follicular phase of the cycle (1–2 days before ovulation) with 10 or 30 mg/kg s.c. or 30 mg/kg p.o. of Onapristone.

Then, the monkeys are paired up. Because of the progesterone determination in the luteal phase, it was noted that ovulation occurred and that the course of the luteal phase was normal. Bleeding (menstruation) occurred as expected on days 27–31 of the cycle. In the case of the treated animals, no pregnancy was noted, but in the case of the control animals, which were treated only with a vehicle, one pregnancy was noted after the pairing.

Other monkeys are treated in the earlier luteal phase (days 1–3 after ovulation) over 3 cycles one time with 10 or 30 mg of Onapristone/kg s.c. or 30 mg/kg p.o. After pairing was completed, no pregnancies were to be observed even after this treatment pattern in the animals that were treated with Onapristone.

Test subjects that exhibit a normal cycle are treated orally on a one-time basis with 100 or 400 mg of Onapristone on the second day before ovulation (LH-2). The hormone profiles (estradiol, progesterone, LH) confirm that ovulation was not inhibited. No significant shortening or lengthening of the cycle was proven.

Other test subjects are orally treated one time with 100 or 400 mg of Onapristone 2 days after ovulation (LH+2). Then, a biopsy of the endometrium is performed 4 and 6 days after ovulation. Histology revealed pronounced changes in the case of the treated females in terms of desynchronization of the endometrium.

Clinical experiments with infertile females indicate that a successful implantation is regarded as improbable especially because of such changes of the endometrium and thus successful implantation is also not to be expected in the case of the females of the treatment group.

What is claimed is:

1. A method for demand-oriented female birth control, comprising administering a single dose of a competitive progesterone antagonist at any point in the menstrual cycle, said dosage being below the ovulation-inhibiting dosage and being effective for birth control.

2. A method of claim 1, wherein the competitive progesterone antagonist is:

11β-[4-N,N-Dimethylamino)phenyl]-17α-hydroxy-17β-(3-hydroxypropyl)-13α-methyl-4,9(10)-gonadien-3-one, 11β-[4-acetylphenyl]-17β-hydroxy-17α-(3-hydroxyprop-1(Z)-enyl)-4,9(10)-estradien-3-one, 11β,19-[4-(cyanophenyl)-o-phenylene]-17β-hydroxy-17α-(3-hydroxyprop-1(Z)-enyl)-4-androsten-3-one, 11β,19-[4-(3-pyridinyl)-o-phenylene]-17β-hydroxy-17α-(3-hydroxyprop-1(Z)-enyl)-4-androsten-3-one, 17α-hydroxy-17β-(3-hydroxypropyl)-11β-[4-(1-methylethenyl)-phenyl]-13α-estra-4,9-dien-3-one, 11β-[4-(3-furanyl)-phenyl]-17α-hydroxy-17β-(3-hydroxypropyl)-13α-estra-4,9-dien-3-one.

(Z)-11β-[4-(dimethylamino)phenyl]-17β-hydroxy-17α-(3-hydroxyprop-1-enyl)estr-4-en-3-one 11β-[4-[[(acetyloxy) imino]methyl]phenyl]-17β-methoxy-17α-(methoxymethyl) estra-4,9-dien-3-one 11β-[4-[[[[(ethoxycarbonyl)oxy]imino]methyl]phenyl]-17β-methoxy-17α-(methoxymethyl)estra-4,9-dien-3-one 11β-[4,(acetyl)phenyl]-19,24-dinor-17,23-epoxy-17α-chola-4,9,20-trien-3-one, or (11β, 17α)-11-[4-(acetyl)phenyl]-17,23-epoxy-19,24-dinorchola-4,9,20-trien-3-one.

3. A method of claim 1, wherein the competitive progesterone antagonist is:

17β-(3-Acetoxypropyl)-11β-[4-N,N-(dimethylamino)phenyl]-17α-hydroxy-13α-methyl-4,9(10)-gonadien-3-one, or 17β-(3-benzoyloxypropyl)-11β-[4-N,N-(dimethylamino)phenyl]-17α-hydroxy-13α-methyl-4,9(10)-gonadien-3-one.

4. A method of claim 1, wherein the competitive progesterone antagonist is administered as a pharmaceutical composition further comprising a pharmaceutically acceptable carrier for local, topical, enteral, or parenteral delivery.

5. A method of claim 1, wherein the competitive progesterone antagonist in the dosage unit that is to be administered on a one-time basis is contained in an amount of 1 to 400 mg or is released from the latter in an amount of 1 to 400 mg.

6. A method of claim 1 wherein the progesterone antagonist is dissociated.

7. A method of claim 1 wherein said administration is pre-coital.

8. A method of claim 1 wherein said administration is post-coital.

9. A method of claim 7 wherein said administration is up to 6 hours before coitus.

10. A method of claim 7 wherein said administration is up to 24 hours after coitus.

* * * * *

UNITED STATES PATENT AND TRADEMARK OFFICE
CERTIFICATE OF CORRECTION

PATENT NO. : 6,143,754
DATED : November 7, 2000
INVENTOR(S) : Chwalisz et al.

It is certified that error appears in the above-identified patent and that said Letters Patent is hereby corrected as shown below:

Column 6,
Line 58, reads "en-3-one" should read -- en-3-one, --
Line 60, reads "dien-3-one" should read -- dien-3-one, --
Line 63, reads "one" should read -- one, --

Signed and Sealed this

Nineteenth Day of February, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.     : 6,143,754
DATED          : November 7, 2000
INVENTOR(S)    : Kristof Chwalisz et al.

It is certified that error appears in the above-identified patent and that said Letters Patent is hereby corrected as shown below:

<u>Title page,</u>
Please add the following Items:
Item -- [22] PCT Filed:       October 24, 1995 --
Item -- [86] PCT Number:      PCT/EP95/04191 --

Signed and Sealed this

Twenty-seventh Day of May, 2003

JAMES E. ROGAN
*Director of the United States Patent and Trademark Office*